(12) United States Patent
Vilsmeier

(10) Patent No.: US 6,873,867 B2
(45) Date of Patent: Mar. 29, 2005

(54) REFERENCING OR REGISTERING A PATIENT OR A PATIENT BODY PART IN A MEDICAL NAVIGATION SYSTEM BY MEANS OF IRRADIATION OF LIGHT POINTS

(75) Inventor: Stefan Vilsmeier, Kufstein (AT)

(73) Assignee: BrainLAB AG, Kirchheim (DE)

( * ) Notice: Subject to any disclaimer, the term of this patent is extended or adjusted under 35 U.S.C. 154(b) by 489 days.

(21) Appl. No.: 09/827,253

(22) Filed: Apr. 5, 2001

(65) Prior Publication Data

US 2002/0002330 A1 Jan. 3, 2002

(30) Foreign Application Priority Data

Apr. 5, 2000 (EP) ............................................ 00107088

(51) Int. Cl.[7] ............................ A61B 5/05; A61B 19/00
(52) U.S. Cl. ....................................... 600/415; 606/130
(58) Field of Search ................................ 600/415, 414, 600/416, 417, 427, 418, 429, 420, 426, 421, 425, 436, 431; 436/173; 324/307, 308, 309; 378/21; 606/130

(56) References Cited

U.S. PATENT DOCUMENTS

| | | | | |
|---|---|---|---|---|
| 4,597,380 A | | 7/1986 | Raif et al. | |
| 5,417,212 A | * | 5/1995 | Szeles | 600/422 |
| 5,681,327 A | * | 10/1997 | Heywang-Koebrunner | 606/130 |
| 5,706,811 A | * | 1/1998 | Takeda et al. | 600/417 |
| 5,851,183 A | | 12/1998 | Bucholz | |
| 5,891,158 A | * | 4/1999 | Manwaring et al. | 606/130 |
| 6,006,126 A | | 12/1999 | Cosman | |
| 6,143,003 A | * | 11/2000 | Cosman | 606/130 |
| 6,165,181 A | * | 12/2000 | Heilbrun et al. | 606/130 |
| 6,264,665 B1 | * | 7/2001 | Yu et al. | 606/130 |
| 6,421,551 B1 | * | 7/2002 | Kuth et al. | 600/410 |

FOREIGN PATENT DOCUMENTS

| | | |
|---|---|---|
| DE | 196 39 615 A 1 | 4/1998 |
| WO | 91/04711 | 4/1991 |
| WO | 96/10205 | 4/1996 |
| WO | 99/38449 | 8/1999 |

* cited by examiner

Primary Examiner—Daniel Robinson
(74) Attorney, Agent, or Firm—Renner, Otto, Boisselle & Sklar, LLP

(57) ABSTRACT

A method for referencing a body part in a camera-assisted, medical navigation system including the following steps: manually manipulating a light beamer to sequentially produce a plurality of light marks on a surface of the body part; using a plurality of cameras to scan the surface of the body part, wherein the plurality of cameras detect the plurality of light marks; determining three-dimensional spatial positions for respective sequential light marks; and referencing or registering the body part based on the three dimensional spatial positions of light marks.

19 Claims, 1 Drawing Sheet

REFERENCING OR REGISTERING A PATIENT OR A PATIENT BODY PART IN A MEDICAL NAVIGATION SYSTEM BY MEANS OF IRRADIATION OF LIGHT POINTS

BACKGROUND OF THE INVENTION

1. Technical Field

The present invention relates to a method and an apparatus for referencing or registering a patient or a patient body part in a camera-assisted, medical navigation system.

Surgical operations or radiotherapy are nowadays being performed increasingly with the aid of so-called navigation or tracking systems. In this connection, patient data determined by an imaging technique, for example, by a computer tomography or magnetic nuclear resonance tomography, which is employed to indicate to the treating doctor by means of a display output where his treatment tool is momentarily located. One example application consists, for instance, of displaying the position of the tip of an instrument within a part of the body to be treated in order to be able to precisely operate at the places to be treated.

To enable such a navigation system to function, the momentary location of the patient or the part of the body to be treated needs to be known in situ during treatment. This updated positional data can then be assigned to the data received from the imaging process, for example, the data from a computer tomograph produced some time prior to treatment. After this assignment, the computer-assisted treatment may commence.

2. Description of Related Art

In accordance with the prior art, the aforementioned assignment is achieved with the aid of markers, i.e. with the aid of artificial or natural landmarks on the patient. Thus, German patent No. 196 39 615 proposes sticking artificial markers to the skin of the patient prior to a tomographic scan, use being made of markers which are visible in the tomographic image. After tomography, the patient is brought into the operating room. Upon commencement of treatment, referencing of the patient or his body part occurs in that the markers applied thereto are located by a pointer tool, trackable in the navigation system, in order to make their momentary position known to the computer-assisted system. Once the position of the markers is known, the position of all other points from the tomographic data set can be detected in the updated position of the patient and navigation-assisted treatment can commence.

However, the employment of such externally applied markers to the surface of the skin harbors several disadvantages. For one thing, the skin surface is easily shiftable and such shifts result in inaccuracies during referencing. In particular, when targeting the markers with the pointer tool, the skin may be slightly displaced.

Not too many artificial markers may be employed, however, to compensate such inaccuracies since this delays referencing unnecessarily. Invasive solutions, for example, attaching the markers to the bone substance under the skin, are unpleasant for the patient, while natural landmarks, like for example the root of the nose, often cannot be referenced with good positional accuracy.

Another disadvantage of the above-cited method is especially apparent when the treatment is not performed directly after tomography. Thus, for instance, some of the markers may become detached overnight, which can lead to serious difficulties during referencing. One particularly disadvantageous case materializes when the detached markers are replaced by the patient himself at some other location, which may even result in false treatment.

A further navigation system, based on providing reference markers, is known from U.S. Pat. No. 5,383,454, the system employing actively emitting markers, which are provided separately, and likewise result in the disadvantages as described above.

SUMMARY OF THE INVENTION

It is an object of the present invention to provide a method and an apparatus for referencing a patient or a patient body part in a camera-assisted, medical navigation system, which overcomes the disadvantages cited above regarding the prior art. In particular, the intention is to make possible an exact means of referencing, which is not susceptible to failure and can be performed simply.

This object is achieved in accordance with the invention by a method for referencing or registering a patient or a patient body part in a camera-assisted, medical navigation system comprising the following steps:

the patient body part to be referenced is brought into the detecting range of a navigation system assisted by at least two cameras, this navigation system detecting with computer support the three-dimensional, spatial positions of light marks, light marks are generated on the surface of the part of the body to be referenced by means of a light beam, the three-dimensional position of the light marks being determined by the camera-assisted navigation system, and the three-dimensional position of the surface of the part of the body to be referenced is determined by means of the positional data for the light marks.

In other words, the present invention is a departure from applying separate markers to the surface of the patient body part, it instead producing these markers simply by beaming light on the surface (of the skin, bone) to produce a spot of light on the surface, which is just as visible to the cameras as the reflection of a marker. When this surface is then scanned by the light beam, practically a plurality of light marks is generated and the composition of these light marks, respectively known as three-dimensional light spots in space, results in a crowd or cloud of spots assigned to the surface of the body part to be treated. Theoretically, detecting just three spots is sufficient, however, the method becomes more stable when more spots are generated. A sufficient number of spots provides enough information to enable one to three-dimensionally assign the surface with high accuracy. Tests have shown that already a low number (roughly 20) of light spots produced in this way is sufficient to be able to determine the spatial location of the body part with good accuracy.

In general, it holds that the areas of the patient scanned by the light beam are those which readily permit re-identification in this form in the corresponding data set of the patient, thus also permitting referencing or registering even when patients are scanned by an imaging technique without any accessory items and then already exhibit such accessory items (e.g. tubes in the mouth or nose) during referencing or registering.

The advantage of the present invention, in addition to the high accuracy attainable, lies especially in the fact that it eliminates all the problems resulting from the use of separately applied markers. Referencing now no longer suffers from markers possibly being displaced, shifted or removed. Referencing in accordance with the invention involves practically no unpleasant side-effects for the patient such as, for instance, the distress of markers being affixed or even invasively secured in place. Isolated false light marks or reflections, e.g. "runaways", such as beams reflected on surfaces other than those desired, can be easily corrected by calculation.

Another major benefit of the present invention lies in the fact that, because no separate markers need to be attached, surgery can now be decoupled in time to a major extent from the tomographic scan. Since there is no substantial change in the skin surface of the patient over lengthy periods, it is now possible to still precisely reference the patient several days after the tomographic scan without it being necessary for the patient to retain markers on the skin surface over this long period of time.

In addition, the invention is already of advantage when scanning the patient. Hitherto, special scans (navigation scans) were performed, i.e. scans containing the CT or MR visible markers. The invention now makes it possible—since the scans are done without markers—for one thing, to de-couple the scans in time from the operation, but also to employ any number of scans for navigational purposes. Thus, should a physician establish prior to the operation that a further CT scan done some weeks beforehand would be of help during navigation, it now poses no problem for him to also employ this during navigation, since it is not necessary that markers are imaged in such a scan.

Furthermore, it is particularly of advantage that an already existing camera system can be used by the technology in accordance with the invention, i.e. no additional devices, such as e.g. laser scanners, are needed. Compared to conventional methods, in which detecting or registering of the points is done with a navigation pointer (i.e. the bone surface is scanned with a pointer tip, the respective 3D coordinates of the points are stored, and this cloud of points is then mathematically brought to agree with the surfaces obtained from the CT scan data), the present method in accordance with the invention permits enhanced accuracy and faster detection.

Referencing in accordance with the invention can be employed for any surgery requiring the momentary three-dimensional position of a patient body part to be determined. The invention is, however, in particular suitable for methods in which the three-dimensional position of the surface is assigned to a set of image data, previously produced by an imaging technique, for the body part, especially in a CT, MRI (magnetic nuclear resonance tomograph), PET, SPECT, x-ray or ultrasound scan data set to update-reference the image data of this data set.

It is basically of advantage for proper functioning of the method in accordance with the invention when a clearly discernible light spot is generated on the surface of the patient body part as the light marker. Thus, the beam should be directed as much as possible at its impact location. In this respect, it is particularly of advantage to use a beam of invisible light since the light spot produced thereby can be clearly distinguished from the light reflections generated by the room lighting otherwise illuminating the patient body part. Employing an infrared light beam is of advantage in this respect, the cameras then being set to detect the reflections for this light. Very well defined and directed light marks are obtained by using laser light.

When, as proposed above, invisible light is employed to generate the light marks, it is in principal difficult to establish where the light beam is being beamed at any one time. To solve this problem, the method in accordance with the invention is advantageously carried out so that a visible light reflection is generated on the surface by means of a second beam of visible light, aimed substantially at the same target area as the invisible referencing light beam. With the aid of this second light beam, it is now possible to clearly recognize where the invisible referencing light beam occurs. This second light beam may also be a laser light beam. This embodiment just cited is also of advantage in avoiding danger. As already mentioned above, due to the possibility of generating sharply outlined light marks, it is of advantage to use an invisible laser light beam as the referencing light beam. Since this light beam is invisible to the human eye and accidental beaming into the open eye produces no eyelid blink reflex, there is a risk of injury, such as e.g. retinal burns. However, when a second beam of visible light is used, as proposed in accordance with the preferred embodiment, this can serve, on the one hand, as a target aid, excluding sensitive areas (e.g. the eyes) from radiation, while, on the other hand, this visible light prompts eyelid blink reflex when entering the eye to thus prevent corneal burns.

There are in principle several possibilities of generating the two light beams. Thus, for example, two light sources, located juxtaposed or nested, can be employed. Of course, there is also the possibility of employing a single light source beaming both visible and invisible light.

In another preferred embodiment of the method, several light marks (spots) are generated by the referencing light beam in sequence on the surface, while the position of the generated light marks is detected all the time, i.e. in particular until a sufficient number of positional data for determining the spatial position has been acquired. In this connection, it is also possible to permit the assisting computer to continually check by means of a matching method during referencing whether it already has sufficient light marks for the assignment of referenced amount of spots to the surface from the image data set (e.g. tomograph). When at some point in time sufficient data is available, a visual or acoustical signal can be output to indicate successful referencing.

In another advantageous embodiment of the method in accordance with the invention, the part of the body to be referenced is moved during referencing so that camera shades are eliminated, the movement of the body part being tracked in the navigation system by means of a marker array fixedly positioned relative to the part of the body. Since the cameras are usually fixedly installed, spots would materialize in certain locations located in the camera shade, especially when referencing the face, for example behind a nostril. It is thus of advantage to move the patient when wishing to beam these points with light marks and to map these markers. In order to avoid that this movement falsifies detection, it must be tracked in the navigation system, and this is done with the cited marker array, i.e. for example via a three-armed Mayfield reference adapter with a known marker array.

In accordance with the invention, an apparatus for referencing or registering a patient or patient body part is further provided, including a medical, navigation system assisted by at least two cameras, the navigation system detecting with computer support the three-dimensional, spatial positions of the light marks in a detecting area, and means for generating light marks on the surface of the body part to be referenced, the three-dimensional, spatial position of the light marks being determined by the camera-assisted navigation system, whereby the means for generating the light marks is a light beamer, which produces light reflections on the surface as light marks. The light beamer may be a beamer for invisible light, in particular infrared light, the cameras being set to detect the reflections of this light. Furthermore, the light beamer may be a laser light beamer.

Preferably, the light beamer projects a second beam of visible light, aimed substantially at the same target area as that of the invisible referencing light beam, a visible light reflection being generated in addition on the surface. This second light beamer may also beam visible laser light. In this arrangement, the light sources for the light beamers may be unified into a single light source or they may be two juxtaposed or two nested light sources.

Preferably, the apparatus comprises a marker array, fixedly positioned relative to the body part, by means of which the body part to be referenced is tracked during a movement in the course of referencing to eliminate camera shades.

Inversely, of course, a camera movement may also be tracked. In most cases, it is of advantage when the body part of the patient to be treated remains stationary during treatment and also during referencing or registering. In this case, camera shades can be avoided by changing the position of the cameras themselves. Since the marker array furnishes images from differing camera angles, in this case too, the relative movement between the cameras and the body part can be tracked and taken into account during referencing.

The advantages attainable with the apparatus in accordance with the invention are those as already explained with regard to the method in accordance with the invention.

BRIEF DESCRIPTION OF THE DRAWING

The invention will now be detailed by way of an embodiment with reference to the sole FIGURE illustrating schematically the use of a referencing apparatus in accordance with the invention, by means of which a patient or patient body part is referenced or registered.

DETAILED DESCRIPTION OF THE PREFERRED EMBODIMENTS

Figure 1:
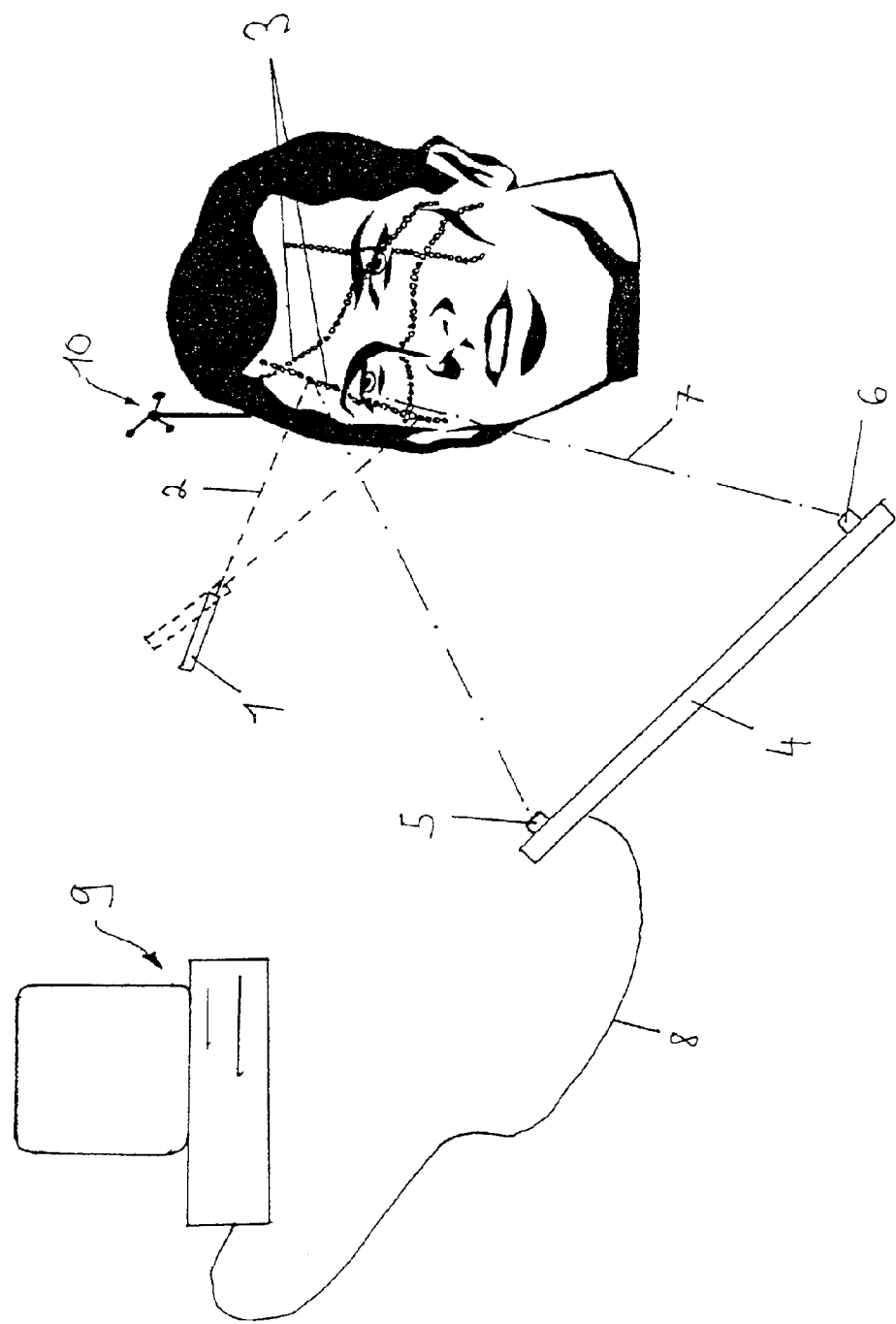

Referring now to the FIGURE, there is illustrated schematically the computer and display of the camera-assisted navigation system, identified as a whole by the reference numeral 9. This computer is connected to the camera mount 4 via the cable connection 8, two infrared cameras 5 and 6 for monitoring the target area being attached to the camera mount spaced away from each other.

In this case, it is the position of the human head shown that is to be referenced or registered. For this purpose, use is made of the light beamer 1, which projects an infrared laser light beam 2 on the facial surface of the patient. The light beamer 1 is indicated by the broken line in a second position to indicate its constant swinging during referencing.

The facial surface is then scanned by the referencing light beam 2, resulting in light reflections or light spots 3 being produced in sequence on the surface. In the drawing, only a few such light marks are represented by way of example, i.e. by a line of such light spots. However, these spots or reflections may also in general be produced individually at suitable locations by beaming.

Before the actual treatment, the person conducting treatment simply takes hold of the light beamer 1 and scans the facial surface with the light beam 2 for some time, Due to the fast recording in sequence of single images, the camera system produce respective light reflections 3 each arranged in sequence, the light path of which for a single light spot is indicated in the drawing by the dot-dash line 7. The two cameras are able to three-dimensionally map the spatial location of the light reflection and the computer system 9 can determine from the data of the detected light marks the position of light spots assigned to the facial surface.

Stored in the computer are the data from a scan of the patient's head, and thus also the data for the facial surface. The computer then continually determines with the aid of a matching routine whether the number of the imaging spots obtained from referencing by means of the light beam is sufficient for it to assign or make congruent the detected surface points of the surface, as known to it from the scan data set. Once sufficient agreement exists, an acoustic and/or visual signal is output to indicate to the person conducting treatment that referencing has been successfully concluded.

The imaging spots 3 generated thus eliminate the need for attached markers or markers otherwise applied, as used hitherto separately. The plurality of light spots 3 obtained makes it possible to perform high accuracy referencing.

Also schematically shown in the figure is that a reference adapter 10 is fixedly positioned to the head of the patient. This adapter comprises three reflectors, the positions of which can be likewise tracked by the cameras 5, 6. Should it now be necessary to turn the head of the patient during referencing or to move the cameras 5, 6, to eliminate camera shades, for instance by the nostril, the relative movement is tracked with the aid of the adapter 10 and taken into account in referencing so that detecting errors are avoided.

As already mentioned, the light beamer 1 may project in addition to the invisible light beam 2 also a visible light beam in the same direction and with the same focus to enable the person conducting treatment to keep visual track of the light spots generated and to prevent beaming into the eyes.

The referencing system in accordance with the invention may be employed with all methods of treatment involving an image-assisted operation. This applies to both surgical operations and radiation treatments. Referencing can also be employed for tracking systems with passive marker arrays as well as for those with active emitter markers, as used for instance in tracking medical instruments. Although hitherto it has mainly been indicated that the light marks are generated by means of the light beam on the skin surface of the patient, it is also conceivable within the scope of the invention to reference bone structures already exposed in this way for treatment, for instance, exposed bone portions of the skull or spine.

In the foregoing description, preferred embodiments of the invention have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A method for referencing or registering a body part in a camera-assisted, medical navigation system comprising the following steps:

manually manipulating a light beamer so as to scan a light beam produced thereby across a surface of the body part to sequentially produce a plurality of light marks on the surface of the body part;

using a plurality of cameras to detect the light marks on the surface of the body part;

determining three-dimensional spatial positions for respective light marks; and referencing or registering the body part based on the three dimensional spatial positions of light marks.

2. The method as set forth in claim 1, wherein the step of referencing or registering the body part includes assigning a set of image data, previously produced by an imaging technique for said body part, to the referenced or registered body part.

3. The method as set forth in claim 1, wherein the plurality of light marks are produced by a beam of invisible light.

4. The method as set forth in claim 3, wherein said light beam is a laser light beam.

5. The method as set forth in claim 3, wherein a visible light reflection is created on said surface by means of a second beam of visible light, aimed substantially at the same target area as that of said invisible light beam.

6. The method as set forth in claim 5, wherein said second light beam is a visible laser beam.

7. The method as set forth in claim 6, wherein said light beams are generated by two juxtaposed or nested light sources.

8. The method as set forth in claim 1, wherein the position of the light marks are continuously detected and determined until a sufficient number of positional data is obtained for registering the body part.

9. The method as set forth in claim 2, wherein the image data includes at least one of CT, MRI, PET, SPECT, X-ray and ultrasound scan data.

10. The method as set forth in claim 3, wherein the invisible light is infrared light.

11. A method for referencing or registering a patient or a patient body part in a camera-assisted, medical navigation system comprising the following steps:

the patient body part to be referenced is brought into the detecting range of a navigation system assisted by at least two cameras, this navigation system detecting with computer support the three-dimensional, spatial positions of light marks, light marks are generated on the surface of the part of the body to be referenced by means of a light beam, the three-dimensional position of the light marks being determined by the camera-assisted navigation system, the three-dimensional position of the surface of the part of the body to be referenced is determined by means of the positional data for the light marks, wherein either the camera arrangement or said body part to be referenced is moved during referencing so that camera shades are eliminated, a relative movement of said body part being tracked in said navigation system by means of a marker array fixedly positioned relative to said body part.

12. A system for referencing or registering a body part in a medical navigation system, comprising:

a manually manipulated light beamer for producing at least one light beam that can be scanned over the surface of the body part to produce a plurality of sequential light marks on the surface of the body part;

a plurality of cameras that detect the light marks and provide positional data related to respective locations of the light marks; and a processor operatively cooled to the plurality of cameras for receiving the positional data from the cameras and executing program code to determine a three-dimensional position in space for respective light marks, and to reference or register the body part based on the three dimensional position of the light marks.

13. The apparatus as set forth in claim 12, wherein said light beamer produces a beam of invisible light.

14. The apparatus as set forth in claim 13, wherein said light beamer includes a laser light beamer.

15. The apparatus as set forth in claim 13, wherein said light beamer produces a second beam of visible light aimed substantially at said same target area as that of said invisible referencing light beam, whereby a visible light reflection can be generated on said surface.

16. The apparatus as set forth in claim 15, wherein said light beamer includes a visible light beamer.

17. The apparatus as set forth in claim 15, wherein the light sources for said beams are unified into a single light source or are two juxtaposed or two nested light sources.

18. The apparatus as set forth in claim 13, wherein the invisible light is infrared light.

19. A method for referencing or registering a patient or a patient body part in a camera-assisted, medical navigation system comprising the following steps:

the patient body part to be referenced is brought into the detecting range of a navigation system assisted by at least two cameras, this navigation system detecting with computer support the three-dimensional, spatial positions of light marks, light marks are generated on the surface of the part of the body to be referenced by means of a light beam, the three-dimensional position of the light marks being determined by the camera-assisted navigation system, the three-dimensional position of the surface of the part of the body to be referenced is determined by means of the positional data for the light marks, wherein relative movement between said body part to be referenced and said camera arrangement is tracked to eliminate camera shades during referencing through use of a marker array fixedly positioned relative to said body part.

* * * * *

UNITED STATES PATENT AND TRADEMARK OFFICE
CERTIFICATE OF CORRECTION

PATENT NO.   : 6,873,867 B2
DATED        : March 29, 2005
INVENTOR(S)  : Stefan Vilsmeier It is certified that error appears in the above-identified patent and that said Letters Patent is hereby corrected as shown below:

Column 7,
Line 4, "position" should read -- positions --.

Column 8,
Line 1, "cooled" should read -- coupled --.

Signed and Sealed this

Thirtieth Day of August, 2005

JON W. DUDAS
*Director of the United States Patent and Trademark Office*